US005503838A

United States Patent [19]
Schmidt et al.

[11] Patent Number: 5,503,838
[45] Date of Patent: Apr. 2, 1996

[54] IODINE BARRIER TEAT DIP

[75] Inventors: William Schmidt, Woodbury; Deborah A. Ihns, St. Paul, both of Minn.

[73] Assignee: Ecolab Inc., St. Paul, Minn.

[21] Appl. No.: 238,976

[22] Filed: May 6, 1994

Related U.S. Application Data

[63] Continuation of Ser. No. 48,379, Apr. 15, 1993, abandoned.

[51] Int. Cl.$^6$ .............................. A01N 25/24; A01N 59/00
[52] U.S. Cl. .............................. 424/407; 424/667; 424/672
[58] Field of Search .................................. 424/407, 667, 424/672

[56] References Cited

U.S. PATENT DOCUMENTS

| | | | |
|---|---|---|---|
| 3,028,299 | 4/1962 | Winicov et al. | 424/667 |
| 3,066,071 | 11/1962 | Akers et al. | 167/53.2 |
| 3,222,252 | 12/1965 | Kraus | 514/873 |
| 3,728,449 | 4/1973 | Cantor et al. | 424/667 |
| 3,911,107 | 10/1975 | Krezanoski | 424/672 |
| 3,993,777 | 11/1976 | Caughman et al. | 424/667 |
| 4,049,830 | 9/1977 | Pugliese | 514/727 |
| 4,113,854 | 9/1978 | Andrews et al. | 424/81 |
| 4,199,564 | 4/1980 | Silver et al. | 514/643 |
| 4,199,602 | 4/1980 | Lentsch | 424/343 |
| 4,258,056 | 3/1981 | Lentsch | 424/303 |
| 4,311,709 | 1/1982 | Dybas et al. | 424/330 |
| 4,376,787 | 5/1983 | Lentsch et al. | 514/576 |
| 4,446,153 | 5/1984 | Yang | 514/730 |
| 5,017,369 | 5/1991 | Marhevka | 514/635 |
| 5,139,788 | 8/1992 | Schmidt | 424/616 |

FOREIGN PATENT DOCUMENTS

| | | |
|---|---|---|
| 1065254 | 10/1979 | Canada . |
| 25640 | 3/1981 | European Pat. Off. . |
| 0473395 | 3/1992 | European Pat. Off. . |
| 2376662 | 8/1978 | France . |
| 3077828 | 4/1991 | Japan . |
| 1144637 | 3/1969 | United Kingdom . |

OTHER PUBLICATIONS

*The Merck Index*, 10th Ed. p. 1095, abstract No. 7458 (1983).
"Postmilking Teat Antisepsis", J. W. Pankey, Symposium on Bovin Mastitis, *Veterinary Clinics of North America: Large Animal Practice*, vol. 6, No. 2 (Jul 1984).
"Efficacy Evaluation of Two New Teat Dip Formulations Under Experimental Challenge", J. W. Pankey et al., *Journal Dairy Science*, 68:462–465 (1985).
"Hygiene in the Prevention of Udder Infections. V. Efficacy of Teat Dips under Experimental Exposure to Mastitis Pathogens", W. N. Philpot et al., *Journal Dairy Science*, 61:956–963 (1978).
"Teat Dip as a Component of Coliform Mastitis Control", R. H. Bennett, *Dairy and Food Sanitation*, vol. 2, No. 3, pp. 110–114 (Mar. (1982).
"Germicidal Teat Dip in a Herd with Low Prevalence of *Streptococcus agalactiae* and *Staphylococcus aureus* Mastitis", R. J. Eberhart et al., *Journal Dairy Science*, 66:1390–1395 (1983).
"The Effect of a Teat Sealer on Coliform Mastitis", R. J. Farnsworth et al, *The Bovine Practitioner*, No. 16, pp. 28–29 (Nov. 1981).
"Use of a Teat Sealer for Prevention of Intramammary Infections in Lactating Cows", R. J. Farnsworth et al, *Journal American Veterinary Medical Association*, vol. 177, No. 5, pp. 441–444 (Sep. 1, 1980).
"Hygiene in the Prevention of Udder Infections. II. Evaluation of Oil–Based Teat Dips", W. N. Philpot et al., *Journal of Dairy Science*, 58:205–216 (1980).
"Control of Mastitis in the Dairy Herd by hygiene and Management", F. K. Neave et al., Journal Dairy Science, vol. 52, No. 5, pp. 696–707.

*Primary Examiner*—Marianne M. Cintins
*Assistant Examiner*—Kevin E. Weddington
*Attorney, Agent, or Firm*—Merchant, Gould, Smith, Edell, Welter & Schmidt

[57] ABSTRACT

A protective aqueous antimicrobial film forming composition that can be applied to dairy animals to form a protective film. The film can be used to reduce the incidence of both contagious and environmental mastitis in dairy herds and can be formed from an aqueous composition that can contain a nonionic iodine complex, a polyvinyl alcohol composition, having a degree of hydrolysis greater than 92%, preferably greater than 98%, and a thickener. The aqueous mixture can be applied to udder and teats of dairy herds to form a protective coating that can prevent infection from staphlococcus, streptococcus, klebsiella and other pathogens. The film can be removed using water in a convenient short period of time permitting efficient milking operations. After milking, the composition can be reapplied to the herd and can protect the herd from mastitis until the herd is again milked. The material of the invention has the property that after application and drying both films and plugs of the protective coating is softened and removed even in cold water in a convenient time frame.

21 Claims, No Drawings

5,503,838

IODINE BARRIER TEAT DIP

This is a continuation of application Ser. No. 08/048,379, filed Apr. 15, 1993, now abandoned.

FIELD OF THE INVENTION

The invention relates to compositions used in the treatment of milking mammals such as cows in a dairy herd. The materials of the invention can be used to prevent or reduce the incidence of environmental or contagious mastitis in a herd undergoing common milking operations. The invention relates to an aqueous composition containing antimicrobial ingredients and film forming polymers, a film on a cow's udders or teats ameliorating the effects of mastitis causing microorganisms, and a method of treating a dairy herd with an aqueous mastitis preventing material.

BACKGROUND OF THE INVENTION

The effective management and maintenance of large dairy herds and the production of diary products has been a major agricultural accomplishment. One of the problems in maintaining large herds is the health of the individual animals. One health problem in individual animals of dairy herds that causes significant economic problems relates to mastitis. Often during milking the animals skin is irritated by automatic milking machines. This irritation, characterized by redness and occasionally areas of broken skin, can be the site of a microbial attack causing mastitis. Animals that contract mastitis must be removed from service resulting in the loss of the dairy output. As a result, a significant amount of attention has been focused on preventing the development of mastitis or treating mastitis in dairy herds.

The dairy farmer is faced with two different types of mastitis infections. Contagious mastitis is spread during the milking process through contact between the animal and dairy equipment that may carry a source of a mastitis pathogen. Contagious mastitis is most easily controlled using germicidal post milking teat dips. Such germicidal dips then kill bacteria that are introduced onto the surface of the animal from the milking machines. The second type of mastitis, environmental mastitis, is caused by contamination of the animal surface by materials from the barn yard environment, fields, barn interior, etc. Such pathogens include *E. coli, Streptococcus uberis*, klebsiella and others. Such contamination occurs as the animal moves through its environment. Environmental mastitis is best treated with a barrier film that protects sensitive tissues from contamination.

In the treatment and prevention of mastitis, the use of protective coatings, formed from aqueous coating systems, on the animals has been an option for many years. One class of the proposed coating materials are simply film barriers formed on the skin surface to prevent contact between vulnerable tissues and the environment. Another class of coating compositions are actively antimicrobial and prevent the incidence of infection in the animal through the presence of an active biocide in the coating. Barrier-type materials simply prevent direct contact between the skin and contagious materials. Barrier-type materials rarely contain antimicrobial materials. The combination of effective germicidal materials with a film forming or a barrier dip formulation would provide the potential for controlling both contagious and environmental mastitis infections.

Among the materials used in barrier-type or film-type teat dips are solubilized liquids, polyvinylpyrrolidone and other vinyl polymers, protein hydrozylate, natural and synthetic gums, water, ethanol, methanol, isopropanol, soluble polymers, unsaturated fatty oils, cellulose derivatives, acrylic polymer lattices, etc. The latex forms a flexible film on the skin which film can be peeled off after moistening the area. However, removal of the film by peeling can be inconvenient and troublesome and can leave small portions of the film on the animal resulting in potential milk contamination. Further, many antimicrobial materials are incompatible with a variety of polymeric or film forming materials. As a result, some of the most effective and otherwise desirable film formers must be formulated without antimicrobials and must rely entirely on barrier effects to prevent mastitis.

In the typical operations of a dairy herd, the herd is brought into a milking station, the udder is washed to remove the barrier film. Any delay in removal of the film can substantially reduce productivity and substantially increase time required to deal with a large herd. Further difficulty in removing the film can cause abrasion or bruising to the animal which can promote mastitis. Preferably, the films are easily removed, in less than 15 minutes, preferably in less than 10 minutes, and most preferably in less than 5 minutes, using water or mild cleaning solutions. While cleaning can be increased using warm solutions, preferably the mastitis barrier films are removed with cold water that is available in most milking operations. In our experimentation with antimicrobial film forming materials we have found that while a variety of materials can form antimicrobial flexible films on animals, the films can be resistant to easy, quick removal. Further, obtaining a stable aqueous film forming antimicrobial barrier teat dip composition that is easily removable provides an additional formulating challenge. The barrier qualities in the teat dip promote the formation of a resilient flexible coating on the skin and often forms a button or plug on the animal in a location such that the material can flow and form a drip on the teat tip before hardening into a button or plug. This hardened material can often pose the most significant problems in removal of the material prior to milking. In summary, combining a barrier coating, ease of removability with a compatible antimicrobial film system is a significant formulating challenge.

The following references are considered to be representative of the state of this art. Typical disclosures of disinfectant after-milking teat dips (aimed at destroying any pathogens remaining on the teats after milking) can be found in British Patent 1 144 637 (Kelco Chemicals, Ltd.), published on Mar. 5, 1969; Meave et al., *J. Dairy Science*, 52:6696 (1969); Dodd et al., "Mastitis Control", *Biennial Reviews* (1970) University of Redding, England, National Institute of Research of Dairying, pp. 21–57; Lentsch, U.S. Pat. No. 4,258,056; Lentsch et al., U.S. Pat. No. 4,376,787; Yang, U. S. Pat. No. 4,446,153; Marhevka, U.S. Pat. No. 5,017,369; Cantor et al., U.S. Pat. No. 3,728,449; Pankey, "Postmilking Teat Antisepsis", Symposium on Bovine Mastitis, Veterinary Clinics of North America: Large Animal Practice, Vol. 6, No. 2, July 1984; Pankey et al., "Efficacy Evaluation of Two New Teat Dip Formulations Under Experimental Challenge", *Journal Dairy Science*, 68:462–465 (1985), Philpot et al., "Hygiene in the Prevention of Udder Infections. V. Efficacy of Teat Dips Under Experimental Exposure to Mastitis Pathogens, *Journal Dairy Science*, 61:956-963 (1978), Bennett, "Teat Dip as a Component of Coliform Mastitis Control, *Dairy and Food Sanitation*, Vol. 2, No. 3, pp. 110–114 (March 1982), Eberhart et al, "Germicidal Teat Dip in a Herd with Low Prevalence of *Streptococcus agalactiae* and *Staphylococcus aureus mastitis*", Journal Dairy Science, 66:1390–1395 (1983).

Typical disclosures of protective or barrier-type teat dips can be found in Acres et al., U.S. Pat. No. 3,066,071, Krause, U.S. Pat. No. 3,222,252, Philpot et al., *Journal Dairy Science*, 58:205–216, Coughman et al., U.S. Pat. No. 3,993,777, Pugliese, U.S. Pat. No. 4,049,830, Silver et al., U. S. Pat. No. 4,199,564, Dybas et al., U.S. Pat. No. 4,311,709 and Andrews et al., U.S. Pat. No. 4,113,854. Still also for examples of such materials, see Farnsworth, *Journal of American Verterinary Medical Association*, 177:441 (1980) and Farnsworth et al., *The Bovine Practitioner*, No. 16, pp. 28–29 (1981). Still further, please review Canadian Patent No. 1,065,254 and European Published Application No. 25,640 (Mar. 25, 1981). A substantial need exists for an antimicrobial and barrier teat dip that can be easily and rapidly removed during milking operations.

BRIEF DESCRIPTION OF THE INVENTION

We have found that the careful formulation of an aqueous material comprising an antimicrobial effective mastitis treating composition, a carefully selected polyvinyl alcohol composition and a thickener provides a teat dip composition that can exhibit film forming properties, antimicrobial properties against the typical contagious mastitis causing pathogens and barrier properties protecting the animal from environmental mastitis. The material can be formulated such that a film is formed that can be easily removed prior to milking. We have found that the intermediate hydrolyzed polyvinyl alcohol materials and preferably the completely and superhydrolyzed polyvinyl alcohol (PVOH) materials preferably form resistant coatings, are compatible with useful antimicrobial materials and can be used to form phase stable, easily applied aqueous compositions. The ease of removal of these materials is a surprise because the increase in degree of hydrolysis of the PVOH materials is known to reduce the water solubility and sensitivity of the material. We have found that the commonly available thickeners for use in typical aqueous compositions in combination with a polyvinyl alcohol characterized as a fully or superhydrolyzed material combines water resistance wear resistance and strong film forming properties of the polyvinyl alcohol to the barrier teat dip along with flexibility resulting from the presence of the thickener. These materials are used in proportions that are compatible with an antimicrobial material that provides protection against a broad spectrum of mastitis pathogens. We believe that selecting the polyvinyl alcohol that is substantially more hydrolyzed than a "partially hydrolyzed polyvinyl alcohol" provides improved environment and water resistance while not sacrificing ease of cleaning for preliminary removal prior to milking. Further, these materials have been shown to be compatible with useful antimicrobials and, in particular, iodine complexes that are most useful in the teat dip environment. The properties of the material can be improved using other additive systems.

The aqueous material of the invention can be used in treating dairy herds. After milking, the material was applied to the skin of the udder and teats to form the antimicrobial barrier coating to prevent or reduce contagious mastitis. The animal is then released into the environment where the material can protect the animal from contamination from the environment but will be resistant to environmental water such as rain, ponds, mud, etc. remaining on the animal for the period between milkings. When the animal returns to the milking site, the antimicrobial barrier coating can be easily removed in 1 to 5 minutes using an aqueous wash. Milking can continue without delay and after milking is finished, the animal can again be treated with the aqueous material forming a new antimicrobial barrier film.

DETAILED DESCRIPTION OF THE INVENTION

Briefly, the novel aqueous coating composition comprises an iodine complex antimicrobial composition, a polyvinyl alcohol polymeric film forming composition having a degree of hydrolysis greater than about 91%, a thickener formulated in an aqueous base. The aqueous material can contain other useful materials in the formulation to enhance the properties of the materials or to add new properties required by the dairy operator. The aqueous composition can be used to form a barrier film having antimicrobial properties on mastitis susceptible skin surface of a dairy animal. The barrier is long lived and flexible, provides barrier properties and is antimicrobial but can be rapidly removed prior to milking using an aqueous wash in typical dairy operations. The material is applied to the dairy animal in a variety of ways. The material can be sprayed, brushed, dabbed, or flooded onto the susceptible site. One common application mode of applying such dips is to place the aqueous composition in a small container with a useful shape adapted to the teat and apply the contained material in the container directly to the dip teat by dipping the teat into the container filled with the aqueous composition. The material dries quickly to form a barrier layer. The barrier layer is flexible and resists cracking. The layer contains the antimicrobial material that kills microorganisms on the skin surface. Such antimicrobial action is important because the milking operation can often spread mastitis causing microorganisms which can under certain circumstances cause inflammation and infection in abraded or affected skin resulting from contact with milking machines during milking operations.

The preferred antimicrobial agent of the invention is an iodine-nonionic complex. Such complexes are used to maintain the iodine material in the film formed from the aqueous composition to prevent creation of substantial quantities of free $I_2$ or other free iodine species and to any accumulation of iodine or iodide in the cow's tissue, body fluids resulting in a concentration of iodine in any dairy product. Such accumulation could be caused by external contact with free iodine.

The nonionic-iodine complex materials of the invention can be made by contacting a source of active iodine with a polymeric nonionic material having large segments of polymeric residues derived from ethylene oxide, propylene oxide or other alkylene oxides in the form of block or heteric polymer chains. Such nonionic materials contain blocks of polyethylene oxide in the form of $(C_2H_4O)_x$ wherein x can range from about 1 to 45; or polypropylene oxide $(C_3H_6O)_x$ wherein y can range from about 1 to 60; and can also contain regions of heteric random polymer containing from about 1 to about 80% of propylene oxide, the balance comprising ethylene oxide and additional reactant materials. The nonionic material can contain multiple blocks of either ethylene oxide, propylene oxide or both and can also optionally contain heteric units of either ethylene oxide or propylene oxide or mixed heteric blocks. Such nonionic materials can be formed as such or can be polymerized on a starting molecule such as an anion, a sodium alcoholate, an alkyl phenate salt, alkyl carboxylic acid salt or other conventional starting material.

A preferred source of active iodine for reaction with nonionic materials to form the nonionic iodine complexes of the invention is a composition comprising iodine in association with an inorganic iodide providing a source of active iodine. Such a source is shown in Winicov, U. S. Pat. No. 3,028,299 or Cantor et al. U.S. Pat. No. 3,728,449, which are incorporated by reference herein. Commonly, at least 0.35 part of iodide ($I^{-1}$) should be present per part of iodine. In the compositions of the invention, the preferred method of introducing iodine in association with iodide is to employ an aqueous concentrate containing about 57% by weight iodine and 20% by weight HI, or 24% by weight NaI. This will provide approximately the minimum ratio of 0.35 part iodide per part of iodine previously indicated to be important. When higher ratios are desired, additional HI or NaI can be incorporated. In a preferred mode, the iodine iodide complexes are formed by reacting in an aqueous medium iodine ($I_2$) with a source of iodide such as sodium iodide or hydriodic acid. The amounts of materials can be adjusted to result in the preferred iodide iodine ratio of at least 0.35:1.

Polyvinyl alcohol (PVOH), a polyhydroxide polymer having a polymethylene backbone with pendent hydroxy groups, is a water soluble synthetic resin. The resin is produced by the hydrolysis of polyvinyl acetate. The theoretical monomer:

does not exist.

Polyvinyl alcohol is one of a limited number in the class of water soluble polymer materials. The resin is commonly available as a dry solid and is available in granular or powder form. The grades of polyvinyl alcohol include a partially hydrolyzed version having a degree of hydrolysis (the percentage of acetate groups removed from the polyvinyl alcohol leaving free hydroxyl groups) from about 87 to about 91%. An intermediate grade of hydrolysis in the polyvinyl alcohol produces a polymer having from about 91 to about 98% removal of acetate groups. A fully hydrolyzed grade of polyvinyl alcohol has from about 98 to about 99.5% of acetate groups removed. A polyvinyl alcohol product called superhydrolyzed PVOH has greater than 99.5% of the acetate groups removed. The degree of hydrolysis has a marked impact on the properties of the material. The partially hydrolyzed material is substantially hydrophilic and is readily soluble in cold water. As the degree of hydrolysis increases, the hydrophilic properties of the material changes in a contra-intuitive manner. One would assume that as the proportion of hydroxyl groups increases (with the increase in degree of hydrolysis) that the materials would become more hydrophilic. In fact, the opposite is true, the increase in the number of hydroxyl groups tends to increase the number of intra and intermolecular hydrogen bonding between hydroxyl groups resulting in a more strongly bonded and coiled polymer molecular resulting in reduced water solubility and increased hydrophobicity. As a result, superhydrolyzed polyvinyl alcohols resist solubilization and are only solubilized in water at relatively high temperature, i.e. the PVOH is cooked into solution.

Polyvinyl alcohol is commonly produced in nominal number average molecular weights that range from about 4,000 to about 100,000. Commonly, the molecular weight of commercial polyvinyl alcohol grades is reflected in the viscosity of a 4 wt % solution measured in centipoise (cP) at 20° C. (Hoeppler falling ball method). Variation of film flexibility, water sensitivity, ease of solvation, viscosity, film strength, adhesion, dispersing power can only be varied by adjusting molecular weight or degree of hydrolysis. Solutions of polyvinyl alcohol and water can be made with large quantities of lower alcohol cosolvents and salt cosolutes and with an number of other small molecular or polymeric additives or active constituents. Further, polyvinyl alcohols can react with aldehydes to form acetyls, can be reacted with acrylonitrile to form cyanoethyl groups and can be reacted with ethylene or propylene oxide to form hydroxyalkylene groups. Polyvinyl alcohols can also be readily crosslinked and can be borated to affect gelation. Such crosslinking or gelation can be achieved using either a covalent crosslinking scheme or using an ionic reversible crosslinking agent. Polyvinyl alcohol is made by first forming polyvinyl acetate or a vinyl acetate containing copolymer such as an ethylene vinyl acetate copolymer, and removing acetate groups using a base catalyzed alkanolysis. A production of polyvinyl acetate or vinyl acetate containing copolymer can be done using conventional polymerization processes which controls ultimate molecular weight. Catalyst selection, temperature, solvent selection, and chain transformation can be adjusted by persons skilled in polymerization arts to control molecular weight and other polymer structural attributes. The degree of hydrolysis is controlled by preventing completion of the alkanols reaction. Polyvinyl alcohols are made in the United States by a variety of vendors including Air Products and Chemicals Inc., dupont and others.

In sharp contrast to the prior art and particularly Marhevka, U.S. Pat. No. 5,017,369, we have found that partially hydrolyzed polyvinyl alcohol forms an inferior mastitis treating composition compared to our invention. We have found that the partially hydrolyzed PVOH is not suitable for a barrier teat dip having antimicrobial properties. We have found that using the partially hydrolyzed polyvinyl alcohol materials, that the resulting materials resist removal under typical conditions resulting in reduced productivity. Further, we have found that the use of the partially hydrolyzed polyvinyl alcohol material results in a teat dip that can be formulated into useful viscosities but often results in excessive dripping and waste of material after application. Further, we have found in our work with the intermediate hydrolysis grades and grades of polyvinyl alcohol at higher degrees of hydrolysis that the materials can be formulated into a material having an acceptable viscosity, little dripping after application but with the formation of a flexible effective barrier coating that additionally provides antimicrobial properties. The preferred polyvinyl alcohol has a degree of hydrolysis greater than 92%, preferably greater than 98%, most preferably greater than 98.5%, and has a molecular weight that falls in the range of between about 15,000 and 100,000, corresponding to a product viscosity of 12–55, preferably between 40,000 and 70,000, corresponding to a product viscosity of 12–25.

The compositions of the invention may also comprise additional stabilizing agents, wetting agents, skin conditioning agents, thickeners, chelating agents and other materials including pigments, dyes, fragrances, etc. Stabilizing agents may be added to the composition of the invention to stabilize the nonionic iodine complex, stabilize pH, prevent oxidation of the organic materials or to prevent phase separation of the aqueous film forming materials.

Chelating agents or sequestrants are useful stabilizing agents in the invention. Commonly available chelating agents can be used in the invention including both inorganic and organic chelating agents. Organic chelating agents include alkyl diamine polyacetic acid, chelating agents such as EDTA (ethylenediamine tetacetic acid tetrasodium salt), acrylic acid and polyacrylic acid type stabilizing agents, phosphonic acid and phosphonate type chelating agents and others. Preferable organic sequestrants include phosphonic acids and phosphonate salts including 1,hydroxy ethylidene-1,1-diphosphonic acid, amino [tri(methylene phosphonic acid)], ethylene diamine [tetra(methylene-phosphonic acid)], 2 phosphonobutane-1,2,4-tricarboxylic acid as well as alkali metal salts, ammonium salts, or alkyl or alkanol amine salts including mono-, di- or triethanol amine salts. Inorganic chelating agents include commonly available polyphosphate materials such as sodium pyrophosphate, sodium or potassium tripolyphosphate along with cyclic or higher polyphosphate species. Preferably, such a sequestering agent is used at a concentration ranging from about 0.05 wt % to about 0.5 wt % of the composition.

Also useful in the composition of the present invention are wetting agents. Wetting agents function to increase the penetrant activity of the antimicrobial composition of the invention into the tissue surface at risk from mastitis causing microorganisms. Wetting agents also tend to, in some instances, increase the activity of the iodine containing compositions to reduce the populations or kill microorganisms. Wetting agents which may be used in the composition of the invention include commonly available anionic surfactants such as carboxylate, sulfonate, and sulfate materials including carboxylate surfactants such as potassium alkyl oxycarboxylates, an alkyl sarcosinates, alkyl benzene sulfonates, alpha olefin sulfonates, and sulfonates with an ester amide or ether linkage. Additionally useful sulfate wetting agents include sulfated alcohol, sulfated alcohol ethoxylates, sulfated alkyl phenols, sulfated carboxylic acid amides and esters, sulfated natural oils and fats as well as agents such as dioctyl ester sodium sulfosuccinic acid.

The compositions of the present invention are also contained in an emollient to lubricate, condition and generally reduce the irritation on the surface of the application which may result either from the antimicrobial agent or from the mechanical action of the milking machine on the surface. Generally, any water soluble or dispersible skin conditioning agent known to those of skill in this art may be used in the present invention. Preferred emollients to be used in the invention include glycerine, propylene glycol and sorbitol. Generally, the emollient within the present invention ranges from about 0.5 to about 20 wt % of the composition preferably about 1 to 10 wt % of the composition.

A dye may also be used in the compositions of the invention to indicate the range of application. Dye or pigment used in the composition of the invention may be any organic or inorganic dye or pigment which is chemically acceptable trace constituent on surfaces to which the composition is applied. Additionally, the dye should be compatible with the resulting mode of products. Generally, dyes which are useful in the composition of this invention include FD & C Yellow Nos. 5 and 6 and others. Although any number of colorants may be used, these dyes are preferred due to their relative acceptability in various solid and liquid food systems. Generally, dyes or pigments used in the invention are present in a concentration ranging from about 0.001 to about 0.01 wt %.

The composition of the invention may also contain various viscosity enhancers or thickeners. The viscosity enhancer or thickener cooperates with the film forming agent to form a barrier film that retains antimicrobial compositions. Further, the thickener causes the aqueous compositions to cling to the surface skin of the animal and enables the composition to resist waste through excessive dripping. The thickener enables the material to remain in place until dry when the barrier layer is formed. The preferred aqueous compatible thickener compositions useful in the invention are those which do not leave contaminating residue on the surface of the application, i.e. constituents which are incompatible with food or other sensitive products or contact areas. Thickeners which may be used in the present invention include natural gums such as xanthan gum. Also useful in the present invention are cellulosic polymers such as carboxy methyl cellulose, carboxy ethyl cellulose, hydroxy ethyl cellulose and others. Generally, the concentration of thickener used in the present invention will be dictated by the desired viscosity required in the final composition.

The aqueous based formulations useful in this dip application are as follows:

|  | Useful (wt %) | Preferred | Most Preferred |
|---|---|---|---|
| Polyvinyl alcohol[1] | 0.1–30 | 0.2–25 | 0.5–10 |
| Buffer | 0.1–20 | 0.1–10 | 0.2–5 |
| Sequestrant | 0.1–20 | 0.1–10 | 0.2–5 |
| Thickener[2] | 0.1–5 | 0.10–2 | 0.1–1 |
| Emollient[3] | 0.1–30 | 0.2–20 | 0.5–15 |
| $I_2$ - nonionic complex[4] | 0.5–20 | 0.2–25 | 1–12 |
| Wetting agents | 0.1–5 | 0.1–2 | 0.1–1.0 |

[1] Degree of hydrolysis greater than 92%, preferably greater than 98%.
[2] Xanthan preferred.
[3] Sorbitol, glycerine.
[4] Provide from 0.1–2 wt % preferably 0.2–1.5 wt % available $I_2$.

In the manufacture of the compositions of the invention, the ingredients are typically blended in large blending equipment adjusted to the appropriate pH and viscosity and stored in available disposable plastic containers. In processing the compositions of the invention, commonly a quantity of acceptable water such as deionized water is added to blending equipment. To the water is slowly added under conditions of agitation and heat if necessary, the polyvinyl alcohol and thickener compositions if required for appropriate viscosity. The aqueous material is agitated until smooth and into the thickened aqueous composition is placed the nonionic iodine antimicrobial complex composition. While the iodine and nonionic can be premixed to form the complex, the complex can be formed in situ.

Aqueous teat dips have been common for use in dairy operations for many years. In the most common application of the material, farmers have introduced a quantity of aqueous material into a suitable sized container for application by dipping to the animal's skin. The practice of post milking application of the materials has been common in an attempt to reduce or ameliorate the undesirable effects of environmental or contagious mastitis. The aqueous compositions and the resulting films of this invention are barrier layers and antimicrobial materials that prevent the contact between the animal skin and microorganisms either from the environment or from other animals. The stability of the compositions, the ability to form effective barrier layers and the ability to provide antimicrobial properties is a surprising result particularly in view of the water sensitivity of polyvinyl alcohol films. One skilled in the art can easily establish the water removability of the films in the invention. The aqueous material can be applied to any hard surface in virtually any form. The hard surface can be dipped into the material to simulate actual application of the composition to animal skin using the common dipping technique. The film thickness will be the result of the viscosity of the material. The material should be formulated such that little dripping occurs after application. One method of testing the film forming, dripping and removability properties of the material involves dipping disposable plastic pipettes into the material and measuring the properties of the resulting films. The larger volume pipettes having a size and shape somewhat smaller than, but approximating the geometry of the common dairy teat is useful. Commonly the removability of the material is estimated by centering the pipette in approximately 140 milliliters of cold (20° C.) water on a stir plate with a stir bar having a consistent agitation rate. The pipette is placed about one inch from the bottom of the beaker. The amount of time to release or solubilize the film on the pipette in a low agitation environment is then observed and recorded. The sensitivity of the films to aqueous materials at a warmer temperature or with other cleaning materials can similarly be estimated.

The materials of the invention are typically used by first using a warm or cold water removal step. The materials are contacted with water either in the dip mode or using towels or other sheet-like removal means. The water in contact with the films soften the films and result in dissolution or dispersion of the film composition in the water. The films are then rapidly removed by wiping or agitation resulting in a cleaned surface which can be then rinsed with further amounts of water to produce a milkable animal. The animal is then attached to automatic milking equipment. Once milk production is completed, the automated milk equipment is removed and the antimicrobial films are put in place by dipping the teat in an appropriate volume of the material in an appropriately shaped container.

The following examples and data provide a basis for understanding the metes and bounds of the invention and provide a best mode.

Example 1

Into an appropriately sized stainless steel container equipped with a mechanical stirrer was placed 1955.4 grams of soft water. Stirring was initiated and into the soft water was placed 4.0 grams of a 50 wt % active aqueous solution of citric acid followed by 3 grams of sodium citrate and 2 grams of sodium iodide. Stirring was continued until the solution was uniform and into the stirred solution was added 18 grams of xanthan (Keltrol) slowly over the period of a few minutes. Stirring was continued until uniform and into the stirred mixture was placed 1600.0 grams of a 10 wt % active aqueous solution of a polyvinyl alcohol having a degree of hydrolysis of about 99% (Elvanol 90-50). In a container separate from the original container, a premix comprising 90.4 parts of nonylphenolethoxylate having 12 moles of ethylene oxide and 19.2 grams of a premix of 24 grams of sodium iodide and 58 grams of iodine in 18 grams of soft water. Into the separate container under agitation is added 200 grams of sorbitol, 100 grams of glycerine and 8.0 grams of a 97 wt % active aqueous solution of a linear alkyl sulfonate. The mixture in the separate container was mixed until uniform and the total premix in the separate container was then added to the first container to complete the preparation of the barrier antimicrobial material. The pH of a 100% solution of the material was 4.04, the iodine content was 0.289%, the Brookfield viscosity using a number 2 spindle at 20° C. was 1350 cP with a specific gravity of 1.025.

Example 1A

Into a suitably sized container equipped with a mechanical agitator is placed 58.81 parts by weight of deionized water. Into the agitated water is slowly added 0.45 part by weight of Keltrol, a xanthan thickener material. The thickener is dispersed into the aqueous mixture and the mixture is agitated until uniform. Into the uniform aqueous solution is then slowly added under conditions of moderate stirring, 40.0 parts by weight of a 10% aqueous solution of a 87% hydrolyzed polyvinyl alcohol material (Elvanol 52-22). When addition is complete and the solution becomes homogeneous, a mixture, formed in a separate container, comprising about 5 parts by weight of sorbitol, 2.26 parts of nonylphenolethoxylate having 12 moles of ethylene oxide and 0.48 part by weight of a premix of 24 grams of sodium iodide and 58 grams of iodine and 18 grams of water, is introduced into the agitated aqueous mass. Agitation is continued until a uniform mixture has formed and the material becomes uniform.

COATING TEST PROTOCOL

Example 1 and Example 1A were evaluated for properties related to its utility as a teat dip including film formation, dripping and removability properties. The evaluations were performed by dipping disposable plastic pipettes upside down into the aqueous products to simulate teat dipping, were hung in the air to dry. Products dried 24 hours were then subject to their evaluation of properties. Comparative Example 1A formed a dark chocolate brown thin aqueous coating which dripped excessively. The major portion of the aqueous material dripped off, but left a thin even film coating. The material of Example 1 produced on the average between 1 and 2 drops from the pipette tips leaving a thick flexible even barrier coating. In order to evaluate the removability of the material, the coated pipettes were dipped upside down in a glass beaker containing 400 milliliters of cold (20° C.) water on a stir plate with a stir bar having low agitation. The pipette was placed 1 inch from the bottom of the beaker. The time to release or removal of the material in the low agitation environment was recorded. The comparative material of Example 1A after 8 minutes and 50 seconds first showed some signs that the films on the side of the pipette began to soften and release. After 18 minutes, the film was fully removed, however the button formed by the dripped material was not removed until 31 minutes had passed. In sharp contrast, the materials of the invention prepared in Example 1 immediately upon introduction into the water cracked and began to release. After 27 seconds, the film was fully removed and the button was removed after 4 minutes and 35 seconds. The laboratory data shown in the specification provides a basis for comparison of the formulations. The test data are comparable for evaluation purposes and predicts field performance. For practical removal purposes the material should be removable from the animal in less than 5 minutes, and preferably substantially less than 2 minutes (i.e) 60 seconds or less.

Example 2

Following the procedure of Example 1, the following Examples 2–2C were prepared as shown in Table I.

TABLE I

|  | Example | | |
|---|---|---|---|
|  | 2A | 2B | 2C |
|  | % | | |
| Water | 90.55 | 88.29 | 87.76 |
| Acid Blue #9 | Trace | Trace | Trace |
| Xanthan gum | 0.45 | 0.45 | 0.4 |
| Elvanol 90-50[1] | 4.00 | 4.00 | 4.00 |

TABLE I-continued

| | Example | | |
|---|---|---|---|
| | 2A | 2B | 2C |
| | | % | |
| Sorbitol | 5.00 | 5.00 | 5.00 |
| NPE-12[2] | — | 2.26 | 2.26 |
| Tri-iodide Premix[3] | — | — | 0.48 |
| Sodium Iodide | — | — | 0.05 |
| | 100.00 | 100.00 | 100.00 |

[1]Polyvinyl Alcohol - 99% hydrolyzed.
[2]Nonylphenolethoxylate (12 moles-EO).
[3]Premix contains 57% iodine and 20% iodide.

Examples 2–2C were evaluated for coating and removability properties using the protocol discussed above. The test results shown below in Table II demonstrate that a cooperative effect between the iodine sources, the nonionic and the polyvinyl alcohol results in surprising levels of coating efficacy and rapid removability. Only Example 2C was acceptable for button removability.

TABLE II

PRODUCT PROPERTIES

| Coating Properties | uneven | even | even |
|---|---|---|---|
| Removability - side coat | 120 sec (had gummy residue) | 75 sec. | 36 sec. |
| Removability - button | >1 hour | >1 hour | 5 min. |

Comparative Example 3

Using a method similar to that set forth in Example 1 and 1A, prototype teat dip materials were manufactured containing a polyvinyl alcohol having a degree of hydrolysis of between 87 and 89%. The preparations are similar to that shown in Example 1 of Marhevka, U. S. Pat. No. 5,017,369. The purpose of these preparations is to further investigate the coating properties, and removability of the side coated button of the materials formed in the experiments described above. The compositions are as follows:

TABLE III

| Water | 90.00 | 93.00 |
|---|---|---|
| Acid Blue #9 | Trace | Trace |
| Xanthan gum | — | — |
| Elvanol 52-22 PVOH 87–89% hydrolyzed | 8.00 | 5.00 |
| Sorbitol | — | — |
| NPE-12 | — | — |
| Tri-iodine Premix | — | — |
| Sodium Iodine | — | — |
| Chlorhexidine Gluconate (20% wt/vol) | 2.00 | 2.00 |
| | 100.00 | 100.00 |
| Coating Properties | Uneven | Uneven (Both Dripping) |
| Removability - Side Coat | 53 sec. | 90 sec. |
| Removability - Button | less than about 12 mins. | greater than about 12 mins. |

The materials were characterized by uneven film formation with excessive dripping and waste of the teat dip preparation. Further, the materials appeared to be difficult to remove. The side coat were removed in 53–90 seconds while the button was not removed until approximately 12 minutes after contact with water. Such coating and removability properties are unacceptable in typical dairy herd production practices.

MICROBIOLOGICAL TESTING

The materials of Example 1 were prepared and tested using standard AOAC sanitizer test methods for microbial kill. The test results for duplicate preparations of Example 1 are shown below in Table IV and Table IVA for a variety of microorganisms.

TABLE IV

Iodine Barrier Teat Dip
3 Day Test

| | Test Organism | Initial Inoculum (cfu/ml) | cfu/ml) | Percent Reduction |
|---|---|---|---|---|
| Example 1[1] | S. aureus | $1.0 \times 10^8$ | <10 | >99.999 |
| | E. coli | $9.0 \times 10^7$ | <10 | >99.999 |
| | Ps. aeruginosa | $7.3 \times 10^7$ | <10 | >99.999 |
| | E. aerogenes | $6.6 \times 10^7$ | <10 | >99.999 |
| Duplicate Preparation[2] | S. aureus | $1.0 \times 10^8$ | <10 | >99.999 |
| | E. coli | $9.0 \times 10^7$ | <10 | >99.999 |
| | Ps. aeruginosa | $7.3 \times 10^7$ | <10 | >99.999 |
| | E. aerogenes | $6.6 \times 10^7$ | <10 | >99.999 |

[1]pH = 4.04; $I_2$ content = 0.2767 wt-%; Brookfield Viscometer-Number 2 spindle, @ 20 rpm = 1500 cP; @ 50 rpm = 720 cP, measured at room temperature.
[2]pH = 4.04; $I_2$ = 0.2889 wt-%; 1350 cP and 710 cP.

TABLE IVA

Iodine Barrier Teat Dip

| | Test Organism | Initial Inoculum (cfu/ml) | Survivor Numbers cfu/ml) | Percent Reduction |
|---|---|---|---|---|
| Example 1 | K. pneumonias | $1.3 \times 10^8$ | <10 | >99.999 |
| | S. dysgalactiae | $1.7 \times 10^7$ | <10 | >99.999 |
| | S. agalactiae | $2.8 \times 10^7$ | <10 | >99.999 |
| | S. uberis | $3.3 \times 10^7$ | <10 | >99.999 |
| Duplicate Preparation | K. pneumonias | $1.3 \times 10^8$ | <10 | >99.999 |
| | S. dysgalactiae | $1.7 \times 10^7$ | <10 | >99.999 |
| | S. agalactiae | $2.8 \times 10^7$ | <10 | >99.999 |
| | S. uberis | $3.3 \times 10^7$ | <10 | >99.999 |

A further experiment was done to evaluate the effect of temperature on the ability of the material to treat or prevent mastitis on a dairy herd. A series of exemplary materials listed below as brands A–E were prepared. The preparations included an iodine nonionic complex of nonylphenol-iodine at about a 9:1 weight ratio of nonionic to iodine, a citrate buffer that maintains the pH of the material between about 3.5 and 4.5 and a variable glycerine level as shown below in the Table.

The porcine skin test procedure used to evaluate the influence of temperature on the efficacy of iodine teat dips was a newly developed modification of the Excised Teat Assay. The procedure was designed to improve the ease, accuracy and reproducibility of a teat dip efficacy evaluation by using sterile lyophilized porcine skin, which provides a consistent skin test surface, rather than an excised teat. The recovery of surviving and potentially attached bacteria were also improved over the technician dependent Excised Teat rinse procedure.

With one exception, efficacy of all dips versus S. aureus was reduced at the lower (4° C.) temperature, most likely a direct result of a decrease in free iodine. The activity of the composition of the invention was not reduced at lower temperature, most likely due to an increase in viscosity.

The higher viscosity of the composition of the invention might also explain the superior germicidal activity, i.e., equivalent to the 1.0% iodine teat dips.

TABLE V

| Commercial Teat Dip | Titratable Iodine | Glycerine Variable | Average Log Reduction v. S. aureus | |
|---|---|---|---|---|
| | | | 24° C. | 4° C. |
| Brand A | 1.0% | 3% glycerine | 3.7 | 3.0 |
| Brand B | 1.0% | 10% glycerine | 4.3 | 3.1 |
| Brand C | 0.5% | 3% emollient | 3.0 | 2.2 |
| Brand D | 0.25% | no emollient | 2.3 | 1.8 |
| Brand E | 0.1% | 1% glycerine | 1.4 | 1.1 |
| Example 1 | 0.25% | barrier | 3.4 | 3.8 |

The porcine skin test procedure used to compare germicidal activity of teat dips with other commercial iodine based teat dips containing from 0.1 to 1 wt % titratable iodine at variable temperatures was performed using the following procedure[3].

[3] The Klenzade porcine skin test method was presented at the February, 1993 National Mastitis Council annual meeting.

A one inch square sterile lyophilized porcine skin, CORE-THIUM™ 2 sold by Johnson & Johnson in the United Kingdom was rehydrated for one hour in sterile distilled water. The rehydrated skin squares were inoculated in duplicate with 5 microliters of a 24 hour broth culture of the microorganism to be tested. The inoculated skin square was permitted to remain in contact with the inoculum for 5 minutes. Thereafter the inoculated skin squares were dipped into the teat dip solution for 10 seconds, and the skin squares were maintained in a vertical position to allow drainage. Once drainage was complete, the skin squares were placed in a sterile petri dish and maintained in a horizontal position. After 5 minutes of contact time the squares were removed from the petri dishes and placed in a tube containing 10 milliliters of appropriate neutralizer. For iodine teat dips, a sodium thiosulfate neutralizer, used in a concentration of slight excess over the amount of iodine present, is used. These samples were mixed on a Vortex mixer and were plated to enumerate survivor population. As a control, a square of sterile lyophilized porcine skin was submerged in sterile water only and treated as above. Note prior to using the Klenzade porcine skin test method, the teat dip and culture should be equilibrated at the temperatures used, namely 4° or 24° C. for a minimum of 4 hours.

While the above specification, Examples and data can be used to understand the technical nature of the invention, the invention can be made in a number of embodiments without departing from the spirit and scope of the invention. The invention resides in the claims hereinafter appended.

We claim:

1. An aqueous protective antimicrobial film forming composition, formulated to reduce the incidence of both contagious mastitis and environmental mastitis in a dairy herd, said composition consisting essentially of, in an aqueous base:

(a) an effective film forming amount of a polyvinyl alcohol composition having a degree of hydrolysis greater than 98.5%;

(b) an effective amount of a polymeric thickener composition; and (c) an effective antimicrobial amount of an antimicrobial iodine-nonionic complex composition;

wherein a film formed from the protective composition can be substantially removed from the treated animal in less than 5 minutes.

2. The composition of claim 1 wherein the polyvinyl alcohol has a molecular weight between about 15,000 and 100,000.

3. The composition of claim 1 wherein the antimicrobial iodine-nonionic complex composition is a complex formed from a polymeric nonionic composition, comprising ethylene oxide, propylene oxide or mixtures thereof, and iodine.

4. The composition of claim 3 wherein the polymeric composition is a polyethylene oxide block, a polypropylene oxide block or a copolymeric segment comprising an ethylene oxide block and a propylene oxide block.

5. The composition of claim 4 wherein the polymeric composition is polyethoxylated alkyl phenol.

6. The composition of claim 1 wherein the thickener is a xanthan thickener.

7. The composition of claim 6 wherein there is about 1 to 10 wt. % of the polyvinyl alcohol and about 0.1 to 1 wt. % of the xanthan thickener.

8. The composition of claim 3 wherein there is about 1 to 12 wt % of the iodine-nonionic complex composition.

9. A method for reduction of contagious mastitis and environmental mastitis in a dairy herd, the method comprising:

(a) applying an aqueous protective antimicrobial film forming composition to an animal in a dairy herd comprising:

(i) an effective film forming amount of a polyvinyl alcohol composition with a degree of hydrolysis greater than about 92 wt %;

(ii) an antimicrobial amount of an iodine-nonionic complex composition; and (iii) a thickener; to form a film on the teat and a plug on the teat end; and (b) when needed, removing said film and plug by contacting the teat with an aqueous wash, substantially removing the protective composition in less than 5 minutes, and wherein an effective amount of a colorant is optionally present in said composition.

10. The method of claim 9 wherein the film and plug are removed prior to milking, and after milking the animal is contacted with the protective composition.

11. The method of claim 9 wherein an effective amount of a colorant to indicate the presence of the composition is present.

12. The method of claim 9 wherein the polyvinyl alcohol has a molecular weight between about 15,000 and 100,000.

13. The method of claim 9 wherein the antimicrobial iodine-nonionic complex composition is a complex formed from a polymeric nonionic composition comprising ethylene oxide, propylene oxide or mixtures thereof, and iodine.

14. The method of claim 9 wherein the polymeric composition is a polyethylene oxide block, a polypropylene oxide block or a copolymeric segment comprising an ethylene oxide block and a propylene oxide block.

15. The method of claim 9 wherein the nonionic composition is an ethoxylated alkyl phenol.

16. The method of claim 9 wherein the thickener a xanthan thickener.

17. The method of claim 9 wherein there is about 1 to 10 wt. % of the polyvinyl alcohol and about 0.1 to 1 wt. % of the xanthan thickener.

18. The method of claim 9 wherein there is about 1 to 12 wt % of the iodine-nonionic complex composition.

19. An aqueous protective antimicrobial film forming composition consisting essentially of, in an aqueous base:

(a) about 0.5–10 wt % of a polyvinyl alcohol composition having a degree of hydrolysis greater than about 99.5%;

(b) about 0.1 to 1 wt % of an organic polymeric thickener; and (c) about 1 to 12 wt % of an antimicrobial iodine-nonionic complex containing 0.1 to 1 wt % available iodine based on the final composition.

20. The composition of claim 19 wherein the iodine-nonionic complex is a complex of iodine and an ethoxylated alkyl phenol having 6–12 carbon atoms in the alkyl group and 5–20 moles of ethylene oxide.

21. The composition of claim 19 wherein the thickener is a xanthan thickener.

* * * * *

UNITED STATES PATENT AND TRADEMARK OFFICE
CERTIFICATE OF CORRECTION

PATENT NO. : 5,503,838

DATED : April 2, 1996

INVENTOR(S) : William Schmidt et al.

It is certified that error appears in the above-identified patent and that said Letters Patent is hereby corrected as shown below:

On column 4, line 55, please delete "$(C_3H_6O)_x$" and substitute therefore --$(C_3H_6O)_y$--

On column 6, line 27, please delete "dupont" and substitute therefore --duPont--

On column 10, line 56, please delete "2-2C" and substitute therefore --2A-2C--

On column 11, line 16, please delete "2-2C" and substitute therefore --2A-2C--

On column 10, line 63, please delete "%" under "2B"

On column 11, line 6, please insert --%-- under "2A"

On column 12, line 40 (column 1), please insert --Batch No.-- before "Test Organism"

UNITED STATES PATENT AND TRADEMARK OFFICE
CERTIFICATE OF CORRECTION

PATENT NO. : 5,503,838

DATED : April 2, 1996

INVENTOR(S) : William Schmidt et al.

It is certified that error appears in the above-identified patent and that said Letters Patent is hereby corrected as shown below:

On column 12, line 41, please delete "pneumonias" and substitute therefore --pneumoniae--

On column 12, line 44, please delete "pneumonias" and substitute therefore --pneumoniae--

Signed and Sealed this

Sixth Day of August, 1996

*Attest:*

BRUCE LEHMAN

*Attesting Officer*  Commissioner of Patents and Trademarks